(12) United States Patent
Cinelli et al.

(10) Patent No.: US 6,365,645 B1
(45) Date of Patent: *Apr. 2, 2002

(54) ADHESIVE FOR APPLICATION OF FUNCTIONAL ARTICLES TO THE SKIN AND COMFORTABLE REMOVAL

(75) Inventors: Fabio Cinelli, Bologna; Peter Coles, Francavilla al Mare; Italo Corzani, Chieti, all of (IT)

(73) Assignee: The Procter & Gamble Co., Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/331,660

(22) PCT Filed: Dec. 22, 1997

(86) PCT No.: PCT/US97/23471

§ 371 Date: Jun. 23, 1999

§ 102(e) Date: Jun. 23, 1999

(87) PCT Pub. No.: WO98/28018

PCT Pub. Date: Jul. 2, 1998

(30) Foreign Application Priority Data

| Dec. 23, 1996 | (EP) | 96120738 |
| Jul. 1, 1997 | (EP) | 97110730 |
| Nov. 20, 1997 | (EP) | 97120337 |

(51) Int. Cl.⁷ .................................................. C08J 3/00
(52) U.S. Cl. ........................................ 523/105; 523/111
(58) Field of Search ........................... 524/270, 277, 524/822, 481, 505, 578; 525/95; 523/105, 111; 428/343, 354, 355 R

(56) References Cited

U.S. PATENT DOCUMENTS

| 4,593,053 A | * | 6/1986 | Jevne et al. ................ 523/11 |
| 4,699,146 A | * | 10/1987 | Sieverding ................ 128/640 |
| 5,071,704 A | | 12/1991 | Fischel-Ghodsian ........ 428/354 |
| 5,445,627 A | | 8/1995 | Mizutani et al. ......... 604/385.2 |
| 5,559,165 A | | 9/1996 | Paul ........................... 523/111 |
| 5,658,270 A | | 8/1997 | Lichstein .................... 604/387 |

FOREIGN PATENT DOCUMENTS

| CH | 643 730 | 6/1994 | ........... A61F/13/16 |
| DE | 1 934 710 | 1/1970 | |
| EP | A-0- 184 470 | 6/1986 | ........... A61L/15/06 |
| EP | 0 611 575 A1 | 2/1994 | ........... A61L/15/58 |
| FR | 2 734 574 | 11/1996 | .......... C09J/133/02 |
| GB | A-2 115 431 | 9/1983 | .............. C09J/3/14 |
| JP | A-55 092306 | 7/1980 | ............. A61K/7/00 |
| JP | A-62 209008 | 9/1987 | ............. A61K/7/00 |
| WO | WO 93/10201 | 5/1993 | .......... C09J/139/04 |
| WO | 16424 | * 6/1995 | .................... 13/58 |
| WO | WO 95/16424 | 6/1995 | ........... A61F/13/58 |
| WO | WO 96/13238 | 5/1996 | ........... A61F/13/56 |
| WO | WO 96/14822 | 5/1996 | ............. A61K/7/00 |

* cited by examiner

*Primary Examiner*—Edward J. Cain
*Assistant Examiner*—Katarzyna W. Wyrozebski
(74) *Attorney, Agent, or Firm*—Peter D. Meyer; Leonard W. Lewis

(57) ABSTRACT

The present invention relates to topical adhesives used for the attachment of articles to the skin. The topical adhesive provides secure attachment and is pleasing to the skin upon application, yet causes no discomfort and a low level of adhesive residue on the skin upon removal. The topical adhesive is selected to have rheological characteristics determined by the relationship between the elastic modulus G' and the viscous modulus G".

18 Claims, No Drawings

ADHESIVE FOR APPLICATION OF FUNCTIONAL ARTICLES TO THE SKIN AND COMFORTABLE REMOVAL

FIELD OF THE INVENTION

The present invention relates to topical adhesives for attachment to the skin. In particular the present invention relates to such topical adhesives which can be employed for application of functional articles to the skin, particularly for the adhesion of functional articles or the improvement of the function of such articles. Functional articles in this context are cosmetic or pharmaceutical delivery articles which provide a substance to the skin such as skin treatment substances, creams, lotions, hormones, vitamins, deodorants, or drugs; alternatively cosmetic or pharmaceutical delivery articles can also provide a substance to emanate away from the skin such as insecticides, inhalation drugs, or perfumes; further the adhesive of the present invention can also be used in functional articles which are not attached to the skin but as a component in articles which require a high residence time on the skin such as decorative cosmetics (lipstick, eye colors, stage make-up) or cleaning article (hand cleaner, face mask, hygienic cleanser especially for pores). The topical adhesive provides secure attachment or increased residence time and is pleasing to the skin upon application, yet causes no discomfort and a low level of adhesive residues on the skin upon removal. This is achieved by selecting the chemical composition and rheological characteristics of the topical adhesives, in particular with reference to the relationship between the elastic modulus G' and the viscous modulus G" of the topical adhesive.

BACKGROUND OF THE INVENTION

The general prior art in the field of topical adhesives for attachment to the skin is particularly developed in the field of band-aids, plasters and bandages. These articles are, however, typically applied in an emergency situation where for example a cut into the skin of the wearer has occurred and absorption of the body liquids emanating from a wound is desired. In this context performance aspects of the absorbent article such as comfortable and easy use and application, painless removal, discreteness are subordinate to criteria such as sterility, healing support, mechanical protection of the wound. Also such wound covering absorbent articles are mostly adhered to skin areas where prior to application of the absorbent article body hair can be removed or where little or no hair grows.

The present invention relates to topical adhesives which are particularly useful to functional articles such as cosmetic or pharmaceutical delivery articles which provide a substance to the skin such as skin treatment substances, creams, lotions, hormones, vitamins, deodorants, or drugs; alternatively cosmetic or pharmaceutical delivery articles can also provide a substance to emanate away from the skin such as insecticides, inhalation drugs, or perfumes; further the adhesive of the present invention can also be used in functional articles which are not attached to the skin but as a component in articles which require a high residence time on the skin such as decorative cosmetics (lipstick, eye colors, stage make-up) or cleaning article (hand cleaner, face mask, hygienic cleanser especially for pores). Such articles are not used for absorption of body liquids. For example attachment of a vitamin plaster to the skin or of an inhalation drug releasing article to the breast can suitably be done by the adhesive of the present invention. Inclusion of the adhesive into decorative cosmetics allows to increase their resistance to wearing off while not creating a removal problem.

Topical adhesives that are used for absorbent articles such as sanitary napkins and pantiliners have generally been disclosed in US statutory invention registration H1602 or WO 96/33683. Some more details of the adhesive have been disclosed in PCT application WO 95/16424. In this document sanitary articles having a topical adhesive which is applied on the wearer facing side of a sanitary napkin along the entire periphery are disclosed. The problem underlying this document is primarily the safe attachment to the skin but mentions also the problems of detachment of such articles after use without causing undue pain to a wearer.

The disclosure of WO 95/16424 includes a detailed analysis of the criteria for the topical adhesive in respect to rheological criteria. However, this document has little regard to the problem of painless removal of such articles since the rheological criteria taught include epilatory, i.e. hair removal, compositions which are commercially available such as STREP MIELE (™) sold in Italy by Laboratori Vaj S.p.A. The adhesives for topical attachment mentioned in WO 95/16424 include also today's pressure sensitive adhesives which are used to attach sanitary napkins to undergarments. Further, this document only identifies static rheological characteristics but is silent as to the dynamic rheological behaviour of a topical adhesive.

In WO 96/13238 a frequency dependent topical adhesive model is disclosed. However, all measurements disclosed, e.g. on page 9, were made at temperatures between −60° C. and +120° C. and at actual frequencies of 0.1 to 100 rad/s. In order to obtain the necessary data at application temperature (about 20° C., typical bath room, i.e. storage temperature) the Williams-Landel-Ferry (hereinafter WLF) equation was used.

This WLF equation is empirical and only valid within certain limits e.g. it cannot be used to extrapolate to temperatures below the glass transition temperature of a polymeric adhesive also the WLF cannot be used on the basis of values obtained below the glass transition temperature. Details about the WLF equation and its applicability can be found in "Principles of Polymer processing" by Z. Tadmor and C. G. Gogos, published by John Wiley & Sons or in "Viscoelastic Properties of Polymers" by J. D. Ferry also published by John Wiley & Son. Since this is already missing from WO 96/13238 the applicability of the disclosed data cannot be assessed.

European Patent Application EP-638 303 discloses the use of a topical adhesive on side cuffs of sanitary napkins in order to keep the cuffs in an upright position. Swiss publication CH-643730 discloses the use of a very long sanitary napkin having chamfered outer edges with a topical adhesive at the four corners of the outer edges in order to provide a topical adhesive area well outside the region of pubic hair growth. Both applications are silent as to the adhesive composition.

Based on the above state of the art it is an objective of the present invention to provide a topical adhesive for secure attachment and painless removal from the skin for functional articles, combined with a reduced amount of residual adhesive that remains on the skin or on the hairs after removal of the topical adhesive composition.

It is yet a further objective of the present invention that the adhesive for topical attachment does not cause a cold or otherwise unacceptable temperature sensation upon application despite a temperature difference of the adhesive in respect to the skin temperature.

In addition to the above objectives of the present invention it is also desirable for topical adhesives to provide additional benefits such as physical protection. Further, topical adhesives which do not affect the natural skin condition, e.g. by being breathable or water vapour transmitting are preferred.

BRIEF DESCRIPTION OF THE INVENTION

The present invention is useful to attach functional articles to the skin or improve the function of such articles when worn on the skin. Functional articles are cosmetic or pharmaceutical delivery articles which provide a substance to the skin such as skin treatment substances, creams, lotions, hormones, vitamins, deodorants, or drugs; alternatively cosmetic or pharmaceutical delivery articles can also provide a substance to emanate away from the skin such as insecticides, inhalation drugs, or perfumes; further the adhesive of the present invention can also be used in functional articles which are not attached to the skin but as a component in articles which require a high residence time on-the skin such as decorative cosmetics (lipstick, eye colors, stage make-up) or cleaning article (hand cleaner, face mask, hygienic cleanser especially for pores). Such articles are non-absorbent for bodily liquids. The article typically has a wearer facing surface and an outside surface. The topical adhesive allows secure attachment of an article to the skin of the wearer and supports the functionality of the articles. The term "functional" in this context means that the article after being placed on the skin fulfills an additional function which is supported or improved by the topical adhesives according to the present invention.

Detailed analysis of the sequence of common situations occurring from the application of a functional article to the time of removal of such an article has shown that specific adhesive characteristics need to be satisfied in order to achieve the desired performance objectives to support the function of the articles, in particular secure initial attachment, secure attachment during use, painless removal at the end and a reduced level of adhesive residues on the skin after removal. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere. The elastic behaviour can be interpreted as an indication of the "hardness" behaviour of the adhesive. Its value is also critical for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal. The relation between the elastic and viscous modulus also gives an indication of the internal cohesiveness of the adhesive, which is in turn related to the possible presence of adhesive residues on the skin after removal of the topical adhesive composition.

In order to provide topical adhesives for functional articles the relation between the elastic modulus and the viscous modulus as well as their dynamic behaviour is of key importance.

The topical adhesive has an elastic modulus at a temperature of 37° C. (100° Fahrenheit) abbreviated $G'_{37}$ and a viscous modulus at a temperature of 37° C. (100° Fahrenheit) of $G''_{37}$. The difference $\Delta(G'_{37}-G''_{37})$ between the elastic modulus $G'_{37}$ at a frequency of 1 rad/sec and the viscous modulus $G''_{37}$ at a frequency of 1 rad/sec is also defined for the topical adhesive. This difference gives an indication of the behaviour of the topical adhesive with respect to the level of adhesive residues left on the skin after removal of the topical adhesive. The adhesive further has a dynamic elastic behaviour defined as $\Delta G'_{37}$ which is the difference of $G'_{37}$ at a frequency of 100 rad/sec and $G'_{37}$ at a frequency of 1 rad/sec and a dynamic viscous behaviour $\Delta G''_{37}$ which is the difference of $G''_{37}$ at a frequency of 100 rad/sec and $G''_{37}$ at a frequency of 1 rad/sec.

The topical adhesive according to the present invention satisfies the following conditions:

$G'_{37}$ (1 rad/sec) is in the range 1500 Pa to 20000 Pa, preferably 1500 Pa to 15000 Pa, most preferably 3000 Pa to 10000 Pa.

$G''_{37}$ (1 rad/sec) is in the range 100 Pa to 15000 Pa, preferably 100 Pa to 10000 Pa, most preferably 300 Pa to 5000 Pa.

the ratio of $G'_{37}$ (1 rad/sec)/$G''_{37}$ (1 rad/sec) is in the range of 3 to 30.

the ratio $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

is not less than 0.5, preferably in the range 0.7 to 3, most preferably in the range 1 to 1.8.

either the ratio of $\Delta G'_{37}/G'_{37}$ (1 rad/sec) is not greater than 1.5, preferably not greater than unity and most preferably not greater than 0.8, or $\Delta G'_{37}$ is not greater than 10000 Pa, preferably less than 5000 Pa, most preferably less than 2000 Pa, or both.

the difference $\Delta(G'_{37}-G''_{37})$ (1 rad/sec) is greater than or equal to 1250 Pa, preferably greater than or equal to 2500 Pa, more preferably greater than or equal to 3500 Pa.

Further preferred conditions are:

the value of the ratio $G'_{37}/G''_{37}$ at least for the frequency range from above 1 rad/s up to 100 rad/s should preferably be 3.3 or above, more preferably 5 or above, most preferably 10 or above, while not exceeding about 30, preferably 20, anywhere in the frequency interval.

the rheological behaviour can also be related to the values of the Glass Transition Temperature Tg. For topical adhesives according to the present invention Tg should preferably be less than −15° C., more preferably less than −20° C. and most preferably less than −25° C.

the rheological behaviour and acceptance of a topical adhesive can also be related to the specific heat capacity. Preferably the specific heat capacity of the topical adhesive is less than 4 J/g/K, more preferably less than 3 J/g/K and most preferably less than 2 J/g/K.

the rheological behaviour and acceptance of a topical adhesive can also be related to the specific heat conductivity of the adhesive. Preferably the specific heat conductivity is as low as possible, preferably between 1 and 0.1 W/m/K, most preferably between 0.6 and 0.1 W/m/K.

Adhesive compositions which satisfy the above criteria can be used as topical adhesives for functional articles or as components in the formulation of functional articles provided they also satisfy the common requirements of being safe for use on human or animal skin during use and generally after disposal of the article.

Often the criteria of hygienic appearance and pleasant feel upon contact are important such that adhesive composition which are transparent or white, and which prevent a cold, unpleasant feeling upon application are preferred.

The above rheological criteria and other considerations can be satisfied by adhesive compositions where the composition comprises from 45%, preferably from 51%, to 99.5% of a plasticising compound or composition which is liquid at 20° C., from 0.5 to 20%, preferably 5% to 15%, of a polymeric compound or composition which is soluble or swellable in the plasticising compound or composition and with a tackifying resin in an amount in the range from 0% to 50% by weight of the composition, preferably from 0% to 600% by weight of the polymeric compound. The plasticising compound or composition is preferably selected from the group consisting of water, alcohols (preferably glycerol), glycols, polyglycols, liquid polybutenes, oil or combinations thereof. The polymeric compound or composition is preferably selected from the group consisting of block-copolymer-thermoplastic-elastomers, styrene-block-copolymers and hydrogenated styrene-block-copolymers, polyacrylics, polyvinyl alcohol, natural gum or gelatines, polyethyleneoxide, polyvinylpyrrolidon (PVP), polyvinylethers, cellulose derivatives, or combinations thereof.

DETAILED DESCRIPTION OF THE INVENTION

Adhesive for Topical Attachment

The topical adhesive according to the present invention is applied directly to the skin. In a particular application the adhesive can be used as a carrier of a function (dispensing of a compound) and for attachment while in other application improvement of the attachment and resistance to rubbing off is desirable. The adhesive according to the present invention is used in the context of functional articles such as cosmetic or pharmaceutical delivery articles which provide a substance to the skin such as skin treatment, substances, creams, lotions, hormones, vitamins, deodorants, or drugs; alternatively cosmetic or pharmaceutical delivery articles can also provide a substance to emanate away from the skin such as insecticides, inhalation drugs, or perfumes; further the adhesive of the present invention can also be used in functional articles which are not attached to the skin but as a component in articles which require a high residence time on the skin such as decorative cosmetics (lipstick, eye colors, stage make-up) or cleaning article (hand cleaner, face mask, hygienic cleanser especially for pores). The word "skin" according to the present invention does relate to the outer surface of the derma of humans or animals.

In order to provide fixation of an article according to the present invention to the skin it is necessary in some applications to provide a certain area on the side of the article which is facing the skin with the topical adhesive; the topical adhesive can be provided in a layer having a preferred pattern and a thickness or caliper that is preferably constant. The layer can be preferably continuous or alternatively discontinuous, e.g. in form of dots, spirals, or stripes. In other applications the topical adhesive is a compound to the composition of the article.

Physical, Rheological and Adhesive Characteristics of a Topical Adhesive

Even though topical adhesives are used like pressure sensitive adhesives on human skin hair and mucous tissues, it is understood that the topical adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguishes a PSA from other substances that can temporarily stick things (as e.g. water between two glass plates could) is the fact that their rheological parameters and especially the Elastic Modulus G' vary greatly with the frequency of applied stresses. More in particular, G' of PSA can increase over some orders of magnitude while the frequency of applied stresses varies from typical bonding frequency to typical debonding frequency, i.e. 1 rad/s to 100 rad/s as indicated below.

As a first consequence, it derives that it is inadmissible to define materials intended for use as "topical adhesives" by giving values of rheological parameters and especially of G' at a fixed value of frequency. This can be misleading because in the absence of other characteristics it will include materials which have no practical value. It is hence necessary that rheological characterisation must be on the base of dynamic considerations.

This not only applies to the Elastic Modulus G' but also to the viscous modulus G" and hence also for tan $(\delta)$=G"/G'. It is well known that typical PSA have not only a high variation of G' across the considered frequencies but also there is an even higher variation of G" which can get close or become even higher than the value of G', i.e. tan $(\delta)$ becomes about or even greater than 1, in particular at the frequencies that are typical of the debonding.

Without wishing to be bound by theory this can be interpreted as meaning that a high fraction of the energy applied for the debonding is dissipated within the adhesive (so it is not effective in causing the debonding) while this fact causes macroscopically the recording of a very high level of adhesive force.

As indicated above materials useful as topical adhesives according to the present invention have rheological characteristics which are measured at a reference temperature of 37° C. (as usual body temperature of humans) and in a range of frequencies. It has been found that upon application of an article such as a vitamin plaster with a topical adhesive the adhesive contact is formed at a low frequency, while debonding happens at the speed of removing the article. This speed is expressed as a frequency of 100 rad/s while the low frequency of forming the adhesive bond has been found to be on the order of 1 rad/s. Therefore, the frequency range for use according to the present invention is between 1 and 100 rad/s.

It is believed that the adhesive bonding characteristics are selected most appropriately at human body temperature. Since the topical adhesive according to the present invention is used directly on skin and the person skilled in the art is directed to select the adhesive composition to have a small specific heat capacity (e.g. preferably less than 4 J/g/K) the actual temperature of the topical adhesive will reach 37° C. very quickly or even be warmed up by a human prior to application.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion which is particularly valuable when using articles which are frequently removed and adhered again or replaced while the material remains soft and capable of gently adhering to skin.

The ratio of $G'_{37}$, (1 rad/sec) over $G''_{37}$ (1 rad/sec) is important to ensure that these two values are balanced upon adhesion to the skin. At the same time the absolute changes of $G'_{37}$ need to be limited within the range of frequencies considered. Hence a value for the ratio of $\Delta G'_{37}$ (i.e. $G'_{37}$ (100 rad/sec)−$G'_{37}$ (1 rad/sec)) over $G'_{37}$ (1 rad/sec) has to be kept small in order to maintain the secure attachment of the topical adhesive without causing discomfort over time or at removal/delamination. This can also be expressed in absolute terms by keeping the $\Delta G'_{37}$ below certain values.

Importantly, the ratio of $$\frac{G'_{37}(100\,\text{rad/sec}) - G''_{37}(100\,\text{rad/sec})}{G'_{37}(1\,\text{rad/sec}) - G''_{37}(1\,\text{rad/sec})}$$

needs to be large enough to ensure that the dynamic behaviour of both the elastic and the viscous module are maintained in a relationship which provides secure adhesion and painless and easy removal.

Further, when considering particularly the removal phase of a topical adhesive composition for attachment of functional articles to the skin of a wearer, it is commonly recognized that good conditions of removal of the topical adhesive are achieved when the adhesive can be easily removed from the skin, and particularly from the hairs that may grow on the skin where the article contacts the wearer's body, without causing pain to the wearer, therefore without sticking too hard upon removal to the skin and hairs of the wearer. Particularly, as is apparent to those skilled in the art, a good removal also implies that the topical adhesive does not leave residual remains on the skin or on the hairs. The difference $\Delta(G'_{37}-G''_{37})$ between the elastic modulus $G'_{37}$ (1 rad/sec) and the viscous modulus $G''_{37}$ (1 rad/sec) of the topical adhesive of the present invention is relevant to the scope of providing a reduced level of adhesive residues on the wearer's skin after removal of the topical adhesive. Such a difference gives in fact an indication on the behaviour of the topical adhesive of the present invention as far as the level of adhesive residues on the skin after removal of the topical adhesive from the wearer's skin is concerned.

Without being bound to any theory, it is believed that the difference between the elastic modulus G' and the viscous modulus G" is a direct measure of the internal cohesiveness of the topical adhesive. Therefore increasing the difference $\Delta(G'_{37}-G''_{37})$, provided the other rheological conditions are satisfied, increases the internal cohesiveness of the topical adhesive, and decreases the possibility that residues of adhesive remain on the skin upon removal of the topical adhesive.

Finally the person skilled in the art will also recognise that the Glass Transition Temperature Tg of the adhesive composition, specific heat capacity, and specific heat conductivity are parameters which are useful to more fully define the group of useful topical adhesives.

The following set of characteristics should be satisfied:

$G'_{37}$ (1 rad/sec) is in the range 1500 Pa to 20000 Pa, preferably 1500 Pa to 15000 Pa, most preferably 3000 Pa to 10000 Pa.

$G''_{37}$ (1 rad/sec) is in the range 100 Pa to 15000 Pa, preferably 100 Pa to 10000 Pa, most preferably 300 Pa to 5000 Pa.

the ratio of $G'_{37}$ (1 rad/sec)/$G''_{37}$ (1 rad/sec) is in the range of 3 to 30.

the ratio $$\frac{G'_{37}(100\,\text{rad/sec}) - G''_{37}(100\,\text{rad/sec})}{G'_{37}(1\,\text{rad/sec}) - G''_{37}(1\,\text{rad/sec})}$$

is not less than 0.5, preferably in the range 0.7 to 3, most preferably in the range 1 to 1.8.

either the ratio of $\Delta G'_{37}/G'_{37}$ (1 rad/sec) is not greater than 1.5, preferably not greater than unity and most preferably not greater than 0.8, or $\Delta G'_{37}$ is not greater than 10000 Pa, preferably less than 5000 Pa, most preferably less than 2000 Pa, or both.

the difference $\Delta(G'_{37}-G''_{37})$ (1 rad/sec) is greater than or equal to 1250 Pa, preferably greater than or equal to 2500 Pa, more preferably greater than or equal to 3500 Pa.

Further preferred conditions are also:

the value of the ratio $G'_{37}/G''_{37}$ at least for the frequency range from above 1 rad/s up to 100 rad/s should preferably be 3.3 or above, more preferably 5 or above, most preferably 10 or above, while not exceeding about 30, preferably 20, anywhere in the frequency interval.

the rheological behaviour can also be related to the values of the Glass Transition Temperature Tg. For topical adhesives according to the present invention Tg should preferably be less than −15° C., more preferably less than −20° C. and most preferably less than −25° C.

the rheological behaviour and acceptance of a topical adhesive can also be related to the specific heat capacity. Preferably the specific heat capacity of the topical adhesive is less than 4 J/g/K, more preferably less than 3 J/g/K and most preferably less than 2 J/g/K.

the rheological behaviour and acceptance of a topical adhesive can also be related to the specific heat conductivity of the adhesive. Preferably the specific heat conductivity is as low as possible, more preferable between 1 and 0.1 W/m/K, most preferably between 0.6 and 0.1 W/m/K.

Chemical and Compositional Characteristics of a Topical Adhesive

In order to provide topical adhesive compositions which satisfy the requirements of the above rheological and physical characteristics of a topical adhesive the following formulation criteria can be used in addition. It should be noted that the most of the compositions useful as topical adhesive have a substantially gel-like structure and are preferably gels. This derives from the fact that:

the prevailing component is the plasticiser which is a material liquid at room temperature a macromolecular or polymeric component is present in minor quantities vs. the plasticiser. It forms, in the preferred embodiments, a three dimensional network caused by physical or chemical links between the molecules. Particularly useful physical links are the ones present in systems containing Block Thermoplastic Elastomers.

More specifically, the compositions typically comprise:

from 0.5 to 20%, preferably 5% to 15%, by weight of a macromolecular polymeric substance or a mixture of such substances soluble or swellable in the below mentioned plasticiser(s). As not limiting examples such macromolecular or polymeric substances can be natural and/or synthetic such as natural gums or derivatives such as natural gums and gelatins, their derivatives and alginates; polyacrilics; polyvinyl alcohol; polyethylene oxide; polyvinylpyrrolidon (PVP) or polyvinylethers, their copolymers and derivatives; cellulose derivatives; Block Copolymer Thermoplastic Elastomers and preferably Styrenic Block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS).

from 45 to 99.5% by weight, preferably from 51 to 99.5% by weight, of a plasticising substance or a mixture of plasticising substances, which are liquid at room temperature. As non-limiting examples the plasticiser can be water, various alcohols (like in particular glycerol), glycols and their ethers, polyglycols, liquid polybutenes, esters such phthalates, adipates, stearates, palmitates, sebacates, or myristates, natural or synthetic oils such as vegetable oils, mineral oils, or combinations thereof.

from 0% to 50% by weight of the composition, preferably from 0 to 600% by weight of the macromolecular polymeric substance of a tackifying resin whose main scope is to tailor the Tg especially in systems based on synthetic polymers.

from 0 to 10% and more preferably form 0 to 5% by weight of substances for facilitating and stabilising the gel and the gel forming process both of hydrophilic or hydrophobic liquid plasticisers. These may be for oily systems, e.g. the fatty acids of $C_8$ to $C_{22}$, their metallic salts and their polyoxo-derivatives; lanolin derivatives; silica; bentonite, montmorillonite and their derivatives; polyamides, waxes or mixtures thereof.

Common additives known in the art as preservatives, antioxidants, anti UV, pigments, mineral fillers, rheology modifiers etc. can also be comprised in quantities up to 10% each.

When chemical crosslinks are formed in the system, a crosslinking agent can be present preferably in quantities up to 5% by weight. Chemical crosslinking can be formed also by mutual neutralisation of polymers having different functionalities as in the reaction between acid polyacrylics and polysaccharides.

The resulting compositions for topical adhesives can be divided into three families according to the nature of the main component, i.e. usually the liquid plasticiser(s):

1) Hydrophobic compositions in which the plasticiser is typically an oil or blend of oils of vegetable or mineral origin and the polymer is usually a synthetic polymer, preferably an elastomer, soluble or swellable in oil(s).

2) Mixed phase compositions in which both hydrophobic and hydrophilic components, possibly in both plasticisers and polymers, form two or more separate phases. In such cases an emulsifier/surfactant is preferably present at a suitable level to form stable emulsions between the incompatible phases. For topical adhesives according to the present invention it is preferably that the hydrophobic components are prevailing vs. the hydrophilic ones.

3) Hydrophilic compositions in which typically the plasticiser is water/glycerol/glycols and the like and/or mixtures thereof and the polymeric phase is of synthetic (e.g. polyacrylics) or natural (e.g. natural gums) origin or mixtures thereof.

It is to stress that, depending on the nature of the functional article a selection of the family has to take place. For most functional articles mixed phases compositions can be preferred. For functional articles with a delivery function the compound to be delivered needs to come out of the topical adhesive composition at different speeds, e.g. perfumes can have a delivery profile which changes from high to lower values while drugs have to be delivered preferably at a constant rate to prevent overdosing. Cosmetics often are lipophilic and moisturizing such that a combination of watery and oily components can be more desirable.

On the other hand, hydrophilic topical adhesives tend to be perceived as cold and wet which upon application to the skin of a human is not in line with typical expectation. Additional problems result from the fact that in particular topical adhesives comprising water as the plasticiser have a tendency to dry out unless they are sealed into an impermeable package.

Application of Topical Adhesive

Functional articles in which the topical adhesive according to the present invention can be used, can be made by any of the ways usual in the art. The functional article in this context defines whether the adhesive is provided to hold a substrate to the skin or whether the adhesive as part of a composition is directly provided to the skin.

The topical adhesive is preferably protected prior to use. This protection can be provided by a release liner such as a treated paper, providing easy release for the selected topical adhesive or by a closed container in which the functional articles are stored.

If possible, the article also provides breathability by being at least water vapour permeable, preferably air permeable to prevent stuffiness. Breathability, if not supported by the topical adhesive as such, can be limited to the area of the article where no adhesive is applied.

In order to evaluate the effect of the difference $\Delta(G'_{37}-G''_{37})$ of topical adhesives according to the present invention on the amount of the adhesive residues that remain on the skin upon removal of the topical adhesive a Residue Test has been developed. In this test the adhesion of a standard substrate, provided with a layer of topical adhesives featuring a given value of $\Delta(G'_{37}-G''_{37})$, is achieved on the skin of the forearm of a wearer, and after successive removal the amount of the adhesive residues that remain on the skin is evaluated.

Residue Test

The Residue Test is utilized to evaluate the amount of adhesive residues that remain on the wearer's skin after removal of a sample provided with a layer of a topical adhesive and previously attached to the wearer's forearm skin. The test specifically evaluates the amount of the adhesive residues as the residual skin stickiness caused by the adhesive residues, in terms of the peak tensile force (N) necessary to detach a standard steel plate adhered to the skin after removal of the sample with the topical adhesive.

Sample Preparation

The test is performed on rectangular samples 50×20 mm made of a polyester film 23 μm thick, such as that sold by Effegidi S.p.A. of Colorno (Parma, Italy), provided on one side with a continuous layer of the selected topical adhesive having a constant thickness of 1.35 mm, applied with an Acumeter Model LH-1 extruder. A release paper is applied to protect the adhesive layer. The samples are prepared individually and tested after one hour from preparation.

Apparatus
1) Climatically controlled Lab.
    Maintenance of 23° C. and 50% Relative Humidity.
2) Instron Limited UK Model 6021 Dynamometer.
    Load cell=10N
    Test speed=1000 mm/min
3) Weight
    1 Kg, cylindrical weight with 44 mm diameter and 82 mm height.
4) Cardboard plate
    Square cardboard plate 60×60 mm.
5) Steel plate
    Rectangular steel plate 50×60 mm with a smooth flat surface and provided with means for connection to the movable clamp of the dynamometer.

Residue Measurement

No special treatment of the wearer's skin is required beyond normal cleaning/washing with water and soap and drying at least two hours before the test to allow equilibrium with the room conditions is reached for the skin. A rectangular area about 10 mm longer and wider than the dimensions of the sample is selected on the inner part of the wearers forearm skin, e.g. by drawing it on the skin with suitable means, said area being centered between the wrist and the elbow, with the long side of the area aligned with the length of the arm. The sample is then applied on the skin by an operator, being centered with respect to the previously defined selected area, and a pressure is exerted on it by positioning by hand the weight on the sample and leaving it there for 30 seconds, with the cardboard plate interposed between the weight and the sample in order to cover the whole surface of the sample.

After removal of the weight and of the cardboard plate the sample is worn by the wearer for one hour, and then the sample with the topical adhesive is removed from the wearer's forearm skin by the operator with a slow and smooth pull, without touching the skin where the sample was applied. The steel plate is connected to the upper movable clamp of the dynamometer so that its flat surface is positioned horizontally, perpendicular to the direction of movement of the clamp, and facing down. The wearer positions his arm horizontally on a suitable support under the moving clamp of the dynamometer, with the selected area of the skin where the sample had been applied positioned directly under the steel plate. The wearer's forearm and the steel plate on the clamp are mutually positioned and oriented in such a way that the steel plate is centered with respect to the selected area on the forearm, with the longer dimensions of the steel plate and of the selected area being parallel, and with the surface of the steel plate and of the forearm skin in the selected area about parallel to each other.

The Instron is operated to move the clamp with the steel plate towards the selected area until full contact between the flat surface of the steel plate and the skin is achieved and to apply a compression force of 9.8 N for 30 seconds, then the clamp is raised and the peak tensile force measured in Newton (N) necessary to detach the steel plate from the selected area is recorded as a measure of the residue amount.

The measurements are performed and averaged on five samples of the same type to ensure a representative residue value to be determined for the sample under investigation.

The amount of adhesive residues left on the skin after removal of the topical adhesive has been evaluated for two different samples A and B provided with two different topical adhesive compositions according to the present invention.

Sample A and Sample B are provided with a layer of topical adhesive according to Composition 1 and Composition 2, respectively, as described hereinbelow.

Composition 1

An oil based composition useful on sanitary napkins according to the present invention was prepared using 9.9% by weight of Kraton G-1651, a Styrene/Ethylene-Butylene/Styrene block copolymer containing 33% by weight styrene and available from Shell Co., and 59.3% by weight of Kaydol, a paraffinic mineral oil available from Witco Co.

Moreover the composition contained 301 parts of tackifying resin per 100 parts of Kraton polymer. The tackifying resin was Escorez 5300, a hydrogenated resin available from Exxon Co.

Magnesium Stearate, available from Carlo Erba S.p.A., was used a co-gelifying agent for oil at a level of 0.7% by weight.

Irganox 1010, an antioxidant available from Ciba-Geigy, was added at a level of 0.3% by weight.

So finally the formulation had the following percent composition:

| | |
|---|---|
| Kraton G-1651 | 9.9% by weight |
| Kaydol | 59.3% by weight |
| Escorez 5300 | 29.8% by weight |
| Magnesium Stearate | 0.7% by weight |
| Irganox 1010 | 0.3% by weight |

The composition showed the following rheological properties at 37° C.
a) Elastic Modulus at 1 rad/s, $G'_{37}$=6876 Pa
b) Viscous Modulus at 1 rad/s, $G''_{37}$=550,5 Pa
c) Ratio of Elastic and Viscous Modulus at 1 rad/s, $G'_{37}/G''_{37}$=12.49
d) Ratio of $$\frac{G'_{37}(100\,\text{rad/sec}) - G''_{37}(100\,\text{rad/sec})}{G'_{37}(1\,\text{rad/sec}) - G''_{37}(1\,\text{rad/sec})} = 1.22$$

e) The ratio of $\Delta G'_{37}$ over $G'_{37}$ (1 rad/s) was 0.308, with $\Delta G'_{37}$=2124 Pa.

Composition 2

The topical adhesive is an oil based composition containing 10% by weight of Kraton G-1651, a Styrene/Ethylene-Butylene/Styrene block copolymer available from Shell Co., 49% by weight of Kaydol, a paraffinic mineral oil available from Witco Co., 40% by weight of Escorez 5300, a hydrogenated tackifying resin available from Exxon Co., 0.7% by weight of Magnesium Stearate, a co-gelifying agent for oil available from Carlo Erba S.p.A., and 0.3% by weight of Irganox 1010, an antioxidant available from Ciba-Geigy.

So finally the formulation had the following percent composition:

| | |
|---|---|
| Kraton G-1651 | 10.0% by weight |
| Kaydol | 49.0% by weight |
| Excorez 5300 | 40.0% by weight |
| Magnesium Stearate | 0.7% by weight |
| Irganox 1010 | 0.3% by weight |

The composition has the following rheological properties at 37° C.
a) Elastic Modulus at 1 rad/s, $G'_{37}$=7038 Pa
b) Viscous Modulus at 1 rad/s, $G''_{37}$ =487 Pa c) Ratio of Elastic and Viscous Modulus at 1 rad/s, $G'_{37}/G''_{37}=14.45$ d) Ratio of $$\frac{G'_{37}(100\,\text{rad/sec}) - G''_{37}(100\,\text{rad/sec})}{G'_{37}(1\,\text{rad/sec}) - G''_{37}(1\,\text{rad/sec})} = 1.11$$

e) The ratio of $\Delta G'_{37}$ over $G'_{37}$ (1 rad/s) was 0.291, with $\Delta G'_{37} = 2051$ Pa.

The results of the test are summarized in the following table:

| Sample | $\Delta(G'_{37}-G''_{37})$ (Pa) | Residue (N) |
|---|---|---|
| A | 6326 | 0.33 |
| B | 6551 | 0.27 |

The results show that increasing values of the difference $\Delta(G'_{37}-G''_{37})$ correspond to lower amounts of adhesive residues left on the wearer's skin after removal of topical adhesive compositions according to the present invention.

Moreover, the above described topical adhesive compositions according to the present invention have been judged as comfortable for initial application and for removal form sensitive, hairy skin without causing pain.

What is claimed is:

1. A topical adhesive for application of functional articles to the skin, said functional articles being cosmetic or pharmaceutical delivery articles, decorative cosmetics or cleaning articles, said adhesive having an elastic modulus at a temperature of 37° C. (100° F.), $G'_{37}$, a viscous modulus at a temperature of 37° C. (100° F.), G"37, and a difference $\Delta(G'_{37}-G''_{37})$ between said elastic modulus $G'_{37}$ (1 rad/sec) and said viscous modulus $G''_{37}$, said adhesive being selected to have
  $G'_{37}$ (1 rad/sec) in the range 1500 Pa to 20000 Pa;
  $G''_{37}$ (1 rad/sec) in the range 100 Pa to 15000 Pa;
  the ratio $G'_{37}$ (1 rad/sec)/$G''_{37}$ (1 rad/sec) is in the rage 3 to 30;
  the radio $$\frac{G'_{37}(100\,\text{rad/sec}) - G''_{37}(100\,\text{rad/sec})}{G'_{37}(1\,\text{rad/sec}) - G''_{37}(1\,\text{rad/sec})}$$

is not less than 0.5;
  alternatively either $G'_{37}$ (100 rad/sec)–$G'_{37}$ (1 rad/sec) is not greater than 10000 Pa;

or the ratio $$\frac{G'_{37}(100\,\text{rad/sec}) - G'_{37}(1\,\text{rad/sec})}{G'_{37}(1\,\text{rad/sec})}$$

is not greater than 1.5,
  or a combination thereof,
  the difference $\Delta(G'_{37}31\ G''_{37})$ (1 rad/sec) is greater than or equal to 1250 Pa;

said topical adhesive comprising:
  from 45% to 99.5% by weight of a hydrophobic plasticizing compound or composition which is liquid at 20° C.;
  from 0.5% to 20% by weight of a polymeric compound or composition which is solvable or swellable in said plasticizing compound or composition;
  a tackifying resin in an amount of from 0% to 50% by weight of said composition.

2. A topical adhesive according to claim 1, wherein said adhesive is provided as a continuous layer.

3. A topical adhesive according to claim 1 wherein
  said plasticising compound or composition is selected from the group consisting of mineral oil, vegetable oil, or other oil and combinations thereof; and
  said polymeric compound or composition is selected from the group consisting of block-copolymer-thermoplastic-elastomers, styrene-block-copolymers and hydrogenated styrene-block-copolymers.

4. A functional article suitable for use as a cosmetic or pharmaceutical delivery article, a decorative cosmetic or a cleaning article, said functional article comprising a topical adhesive according to claim 1 for application of said functional article to the skin.

5. The method of using a topical adhesive according to claim 1 for application of functional articles to the skin, said functional articles being cosmetic or pharmaceutical delivery articles, decorative cosmetics or cleaning articles.

6. A topical adhesive according to claim 1 wherein:
said adhesive being selected to have
  $G'_{37}$ (1 rad/sec) in the range 1500 Pa to 15000 Pa,
  $G''_{37}$ (1 rad/sec) in the range 100 Pa to 10000 Pa
  the ratio $G'_{37}$ (1 rad/sec)/$G''_{37}$ (1 rad/sec) is in the range 3 to 30;
  the ratio $$\frac{G'_{37}(100\,\text{rad/sec}) - G''_{37}(100\,\text{rad/sec})}{G'_{37}(1\,\text{rad/sec}) - G''_{37}(1\,\text{rad/sec})}$$

is in the range 0.7 to 3,
  alternatively either $G'_{37}$ (100 rad/sec)–$G'_{37}$ (1 rad/sec) is not greater than 5000 Pa, or the ratio $$\frac{G'_{37}(100\,\text{rad/sec}) - G'_{37}(1\,\text{rad/sec})}{G'_{37}(1\,\text{rad/sec})}$$

is not greater than 1,
  or a combination thereof,
  the difference $\Delta(G'_{37}-G''_{37})$ (1 rad/sec) is greater than or equal to 2500 Pa.

7. A topical adhesive according to claim 1 wherein:
said adhesive being selected to have
  $G'_{37}$(1 rad/sec) in the range 3000 Pa to 10000 Pa;
  $G''_{37}$ (1 rad/sec) in the range 300 Pa to 5000 Pa;
  the ratio $G'_{37}$ (1 rad/sec)/$G''_{37}$ (1 rad/sec) is in the range 3 to 30;
  the ratio $$\frac{G'_{37}(100\,\text{rad/sec}) - G''_{37}(100\,\text{rad/sec})}{G'_{37}(1\,\text{rad/sec}) - G''_{37}(1\,\text{rad/sec})}$$

is in the range 1 to 1.8;
  alternatively either $G'_{37}$ (100 rad/sec)–$G'_{37}$ (1 rad/sec) is not greater than 2000 Pa;

or the ratio $$\frac{G'_{37}(100\,\text{rad/sec}) - G'_{37}(1\,\text{rad/sec})}{G'_{37}(1\,\text{rad/sec})}$$

is not greater than 0.8,
  or a combination thereof,
  the difference $\Delta(G'_{37}-G''_{37})$ (1 rad/sec) is greater than or equal to 3500 Pa.

8. A topical adhesive according to claim 1 comprising from 51% to 99.5%, by weight of a plasticising compound or composition which is liquid at 20° C.;

from 0.5% to 20% by weight of a polymeric compound or composition which is solvable or swellable in said plasticising compound or composition;

a tackifying resin in an amount of from 0% to 600% by weight of said polymeric compound.

9. A cosmetic, pharmaceutical, decorative cosmetic or cleaning article delivery system comprising:

a substrate;

a substance; and, a hydrophobic adhesive for application of said delivery article to the skin;

said adhesive having an elastic modulus at a temperature of 37° C. (100° F.), $G'_{37}$, a viscous modulus at a temperature of 37° C. (100° F.), $G''_{37}$, and a difference $\Delta(G'_{37}-G''_{37})$ between said elastic modulus $G'_{37}$ (1 rad/sec) and said viscous modulus $G''_{37}$, said adhesive being selected to have $G'_{37}$ (1 rad/sec) in the range 1500 Pa to 20000 Pa;

$G''_{37}$ (1 rad/sec) in the range 100 Pa to 15000 Pa;

the ratio $G'_{37}$ (1 rad/sec)/$G''_{37}$ (1 rad/sec) is in the range 3 to 30;

the ratio $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

is not less than 3;

alternatively either $G'_{37}$ (100 rad/sec)–$G'_{37}$ (1 rad/sec) is not greater than 10000 Pa;

or the ratio $$\frac{G'_{37}(100 \text{ rad/sec}) - G'_{37}(1 \text{ rad/sec})}{G'_{37}(1 \text{ rad/sec})}$$

is not greater than 1.5, or a combination thereof, the difference $\Delta(G'_{37}-G''_{37})$ (1 rad/sec) is greater than or equal to 1250 Pa.

10. A delivery system as claimed in claim 9 wherein said adhesive is protected prior to use, wherein said protection is selected from the group consisting of a treated paper release liner and a closed container.

11. A delivery system as claimed in claim 9 wherein said substance is selected from the group comprising skin treatment substances, creams, lotions, hormones, vitamins, deodorants, drugs, decorative cosmetics and cleaning articles.

12. A delivery system as claimed in claim 9 wherein said delivery article further comprises a substance that emanates outwardly from the skin.

13. A delivery system as claimed in claim 12 wherein said outwardly emanating substance is selected from the group comprising insecticides, inhalation drugs and perfumes.

14. A delivery system as claimed in claim 9 wherein said delivery article provides breathability by being water vapor permeable.

15. A delivery system as claimed in claim 9 wherein said delivery article is permeable to air.

16. A delivery system as claimed in claim 9 wherein said said topical adhesive comprises:

from 45% to 99.5% by weight of a hydrophobic plasticizing compound or composition which is liquid at 20° C.;

from 0.5% to 20% by weight of a polymeric compound or composition which is solvable or swellable in said plasticizing compound or composition;

a tackifying resin in an amount of from 0% to 50% by weight of said composition.

17. A delivery system as claimed in claim 16 wherein said plasticizing compound or composition is selected from the group consisting of, mineral oil, vegetable, other oil and combinations thereof.

18. A delivery system as claimed in claim 16 wherein said polymeric compound or composition is selected from the group consisting of block-copolymer-thermoplastic-elastomers, styrene-block-copolymers and hydrogenated styrene-block-copolymers.

* * * * *